(12) United States Patent
Nakayama et al.

(10) Patent No.: US 8,093,412 B2
(45) Date of Patent: Jan. 10, 2012

(54) METHOD OF PURIFYING PROPYLENE OXIDE

(75) Inventors: Toshio Nakayama, Sodegaura (JP); Junpei Tsuji, Chiba (JP); Noriaki Oku, Ichihara (JP); Koji Shinohara, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 77 days.

(21) Appl. No.: 11/570,615

(22) PCT Filed: Jun. 21, 2005

(86) PCT No.: PCT/JP2005/011700
§ 371 (c)(1),
(2), (4) Date: May 24, 2007

(87) PCT Pub. No.: WO2006/001407
PCT Pub. Date: Jan. 5, 2006

(65) Prior Publication Data
US 2008/0035468 A1 Feb. 14, 2008

(30) Foreign Application Priority Data

Jun. 23, 2004 (JP) ................................ 2004-184623
Oct. 29, 2004 (JP) ................................ 2004-315477

(51) Int. Cl.
*C07D 301/32* (2006.01)

(52) U.S. Cl. ........................................ 549/541

(58) Field of Classification Search ................... 549/541
See application file for complete search history.

(56) References Cited

U.S. PATENT DOCUMENTS

| 3,607,669 A | 9/1971 | Jubin, Jr. |
| 3,843,488 A | 10/1974 | Schemidt |
| 4,140,588 A | 2/1979 | Schmidt |
| 5,133,839 A | 7/1992 | Shih |
| 5,139,622 A | 8/1992 | Marquis et al. |
| 7,285,187 B2 * | 10/2007 | Oku et al. .................. 203/3 |
| 2003/0144535 A1 | 7/2003 | Teles |
| 2003/0146080 A1 | 8/2003 | Teles |
| 2007/0032671 A1 | 2/2007 | Shinohara et al. |

FOREIGN PATENT DOCUMENTS

| EP | 4 53084 A | 4/1991 |
| JP | 2003-238547 A | 8/2003 |
| JP | 2003-238548 A | 8/2003 |
| WO | WO 2005/028461 A1 | 3/2005 |

* cited by examiner

Primary Examiner — Taylor Victor Oh
(74) Attorney, Agent, or Firm — Sughrue Mion, PLLC

(57) ABSTRACT

A method of purifying propylene oxide, which comprises subjecting the propylene oxide containing methyl formate as an impurity to extractive distillation using a hydrocarbon of 7 to 10 carbon atoms as an extractant with an extractive distillation column, adding water to the distillate from the overhead of the extractive distillation column to conduct oil-water separation, recycling the oil layer separated to the extractive distillation column, removing the aqueous layer outside the system thereby to obtain propylene oxide in which a methyl formate concentration is reduced as a bottom liquid of the extractive distillation column.

7 Claims, 1 Drawing Sheet

US 8,093,412 B2

METHOD OF PURIFYING PROPYLENE OXIDE

TECHNICAL FIELD

The present invention relates to a method of purifying propylene oxide. More particularly, the present invention relates to a method of purifying propylene oxide, which contains eliminating methyl formate from propylene oxide containing methyl formate as an impurity, wherein methyl formate as the impurity is efficiently separated and removed and propylene oxide in which a concentration of methyl formate is reduced, can be obtained.

BACKGROUND ART

There is known a process for obtaining propylene oxide by reacting an organic peroxide, for example, cumene hydroperoxide with propylene in the presence of a epoxidation catalyst.

In this case, oxygen-containing compound such as water, methanol, acetaldehyde, acetone and propionaldehyde, hydrocarbons and the like are produced as by-products in addition to propylene oxide as a target product. Therefore, a purification step for separating and removing these impurities from propylene oxide to obtain high purity propylene oxide become necessary. Purification processes of propylene oxide are disclosed in U.S. Pat. No. 5,139,622, European Patent 1498414 A or the like.

In addition, it is publicly known to subject to extractive distillation using a hydrocarbon as an extractant in purification of propylene oxide. For example, U.S. Pat. No. 3,843,488 discloses that an alkane such as octane is effective for removing hydrocarbons having 6 carbon atoms as impurities. Further, U.S. Pat. No. 3,607,669 discloses that an alkane such as octane is effective for removal of water. Furthermore, U.S. Pat. No. 5,133,839 discloses that a hydrocarbon such as octane is effective for removal of impurities such as methanol, propionaldehyde and acetone.

However, in the conventional techniques, any concrete method for removing methyl formate at high level is not disclosed. There was a problem that this methyl formate in propylene oxide markedly deteriorated a quality of propylene oxide used as a raw material for various chemical products.

DISCLOSURE OF THE INVENTION

An object of the present invention is to provide a method of purifying propylene oxide, which comprises eliminating methyl formate from propylene oxide containing methyl formate as an impurity, wherein methyl formate as the impurity is efficiently separated and removed and propylene oxide in which a concentration of methyl formate is reduced, can be obtained.

Namely, the present invention relates to a process for purifying propylene oxide, which comprises the following steps of:

(1) subjecting propylene oxide containing methyl formate as an impurity to extractive distillation using a hydrocarbon having 7 to 10 carbon atoms as an extractant, (2) adding water to a liquid distillated from the overhead of an extractive distillation column, then separating the resultant into an oil phase and water phase, (3) recycling the oil phase to the extractive distillation column, (4) removing the water phase outside the system, and (5) obtaining propylene oxide in which methyl formate has been reduced as a bottom liquid of the extractive distillation column.

DESCRIPTION OF SYMBOL

Figure 1:
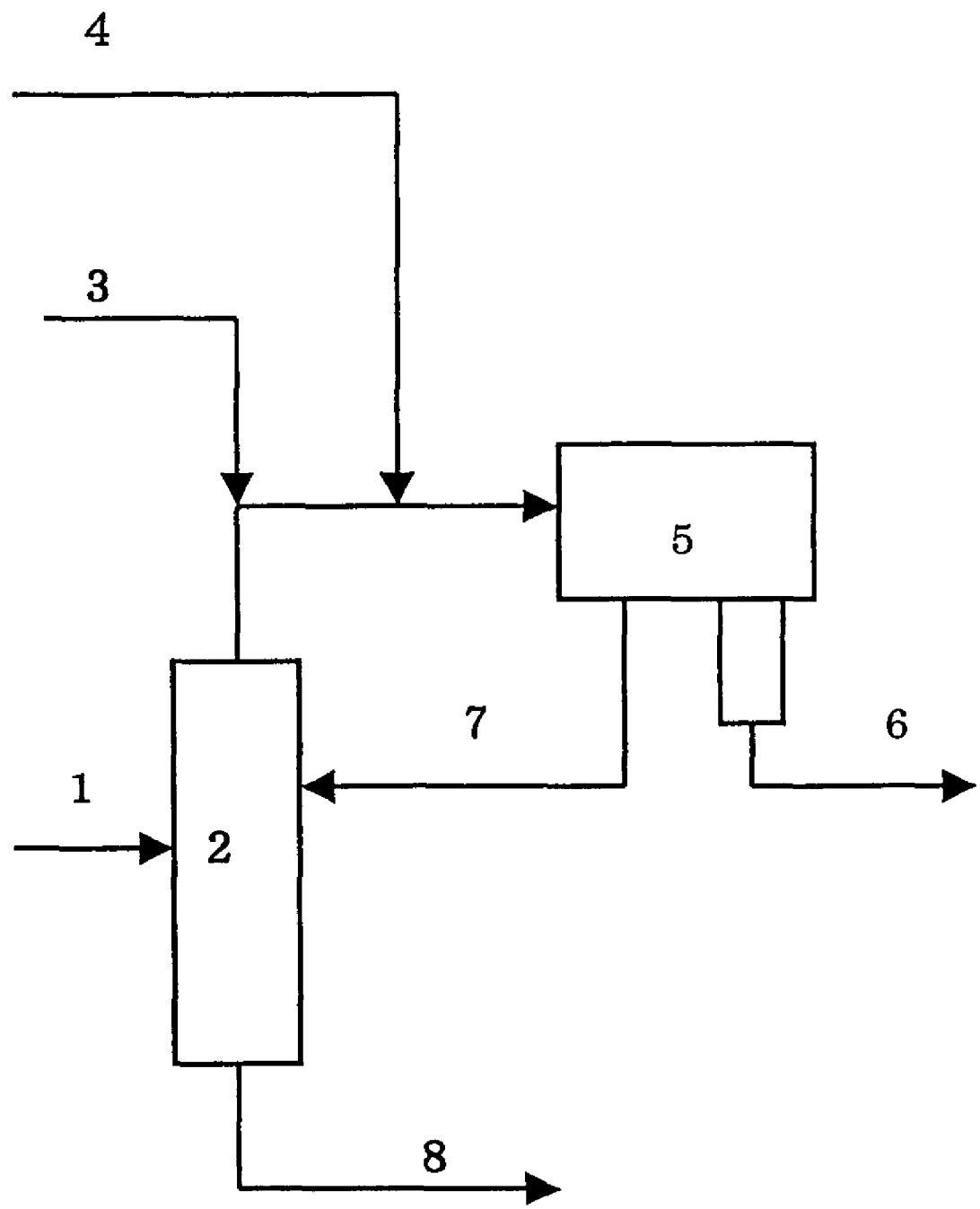
FIG. 1 is a drawing showing one example of flows of the purifying method of the present invention.]

1. Propylene oxide (containing methyl formate as an impurity) to be subjected to purification, 2. An extractive distillation column, 3. A line for supplying an extractant, 4. Water, 5. An oil-water separation apparatus, 6. A water phase after oil-water separation, 7. An oil phase after oil-water separation, 8. A mixed liquid of propylene oxide in which methyl formate has been reduced after purification with the Extractant.

BEST MODE FOR CARRYING OUT THE INVENTION

As propylene oxide to be subjected to purification, there can be exemplified crude propylene oxide obtained by distilling a reaction mixture containing propylene oxide obtained by reacting an organic hydroperoxide such as cumene hydroperoxide with propylene in the presence of an epoxidation catalyst.

The epoxidation is preferably conducted in the presence of an epoxidation catalyst containing a titanium-containing silicon oxide from the viewpoint that the desired product should be obtained under high yield and high selectivity. The catalyst is preferably a catalyst containing titanium chemically bonded to silicon oxide, so-called a titanium-silica catalyst.

For example, products carrying a titanium compound on a silica support, products in which a titanium compound is compounded with a silicon oxide by a co-precipitation or sol-gel method, and titanium-containing zeolite compounds can be listed.

For example, when cumene hydroperoxide as the organic hydroperoxide is exemplified, a reaction of this with propylene can be conducted in a liquid phase using a solvent. The solvent should be liquid under the reaction temperature and pressure, and substantially inert to the reactants and the product. The solvent may be composed of a substance existing in a solution of the hydroperoxide used. When, for example, a cumene solution of cumene hydroperoxide is used as a raw material, it is also possible to use cumene as a solvent without adding a solvent in particular. Other useful solvents include aromatic monocyclic compounds (for example, benzene, toluene, chlorobenzene and o-dichlorobenzene), alkane (for example, octane, decane and dodecane) and the like. The epoxidation temperature is usually 0 to 200° C. and preferably 25 to 200° C. The pressure may be a pressure enough to keep the reaction mixture a liquid state. Usually, the pressure is advantageously 100 to 10000 kPa. The reaction can be advantageously carried out using a catalyst in the form of a slurry or a fixed-bed. The fixed-bed is preferred in the case of a large-scale industrial operation. In addition, the reaction can be carried out by a batch process, a semi-continuous process, a continuous process or the like.

Propylene oxide as a target product, unreacted organic hydroperoxide, unreacted propylene, an alcohol, and a solvent are contained in a reaction mixture obtained by the reaction, further various sorts of by-products are contained as impurities. When cumene hydroperoxide as an organic hydroperoxide and cumene as a solvent are used, a reaction mixture obtained are usually separated into propylene oxide (herein-after, referred to as "crude propylene oxide), unreacted propylene, and cumyl alcohol and the solvent by means of distillation. Besides, unreacted propylene is, for example, recycled, further, cumyl alcohol is converted into cumene via hydrolysis or dehydration-hydrogenation, and recycled, then oxidized in the oxidation step to convert into cumene hydroperoxide. Though the above example was described, the present invention should not be restricted thereto.

Though thus obtained crude propylene oxide can be subjected to purification in the present invention, the present invention should not be restricted thereto.

Crude propylene oxide to be subjected to purification contains methyl formate as an impurity. The content of methyl formate is usually about 30 to about 300 ppm by weight, but should not be limited thereto.

Crude propylene oxide generally contains water, hydrocarbons, oxygen-containing compounds in addition to methyl formate, and such propylene oxide can be subjected to purification in the present invention. Herein, as the hydrocarbons, hydrocarbons having 3 to 7 carbon atoms and as the oxygen-containing compounds, compounds such as methanol, formaldehyde, acetaldehyde, propylene aldehyde, acetone and the like can be exemplified.

When crude propylene oxide is subjected to extractive distillation, an extractant (herein-after, may be referred to as "extractant A") for the extractive distillation preferably includes linear saturated hydrocarbon such as n-heptane, n-octane, n-nonane and n-decane, branched hydrocarbons such as 2,2-dimethylpentane, 2,3-dimethylpentene, 2,2-dimethylhexane and 2,3-dimethylhexane and unsaturated hydrocarbons thereof. Besides, these extractant can be used alone or as a mixture thereof. From the viewpoint of industrial operation, n-heptane easily available industrially is preferable.

The extractive distillation is carried out with an extractive distillation column, as the extractive distillation column, though any type of the column is used and there is no limitation in its structure, packing column, trays column, perforated plate extraction column or the like is generally used. Crude propylene oxide subjected to the extractive distillation is separated into an overhead fraction and bottom fraction.

Water is added to the distillate or gas discharged from the overhead of the extractive distillation column, then, a separation operation is carried out to separate into an oil layer and water layer. The oil layer separated is recycled to the extractive distillation column, on the other hand, water layer separated is removed outside the system. Methyl formate to be eliminated is contained in the water layer and removed therewith outside the system.

Though an used amount of an extractant A, amount of water to be added, and the like can be appropriately determined depending on predetermined conditions and an quality required as a product, in usual, the amount of the extractant is in the range of from 0.25 to 99 times propylene oxide, and the water amount to be added is in the range of from 0.001 to 1 time the extractant. But, these should not be limited thereto. Types and operation conditions of the extractive distillation column can be also appropriately determined in the same manner as described above. For example, the extractive distillation column can be operated under conditions of the number of theoretical plates of 5 to 200, an operation pressure of 0.05 to 5 MPa in terms of absolute pressure and a temperature between 0 to 300° C., but should not be limited thereto.

When water is added to the distillate discharged from the overhead, these are mixed each other. Therefore, a mixing apparatus is not necessarily required, but the mixing apparatus may be used for more sufficient mixing. As the mixing apparatus, a commercially available mixing apparatuses such as a stirrer, a static mixer and a line mixer, are listed. Further, as an oil-water separator used for oil-water separating operation, a common drum or coalescer can be used, and if it can sufficiently separate into oil and water by still standing, it is not particularly limited. A usual drum-type oil-water separator is preferred.

In the above-described way, there can be obtained a liquid containing propylene oxide and the extractant in which methyl formate has been reduced as a bottom liquid of the extractive distillation column.

For example, purified propylene oxide can be obtained by distillation of the bottom liquid, preferably rectification of the bottom liquid because it contains the extractant and other hydrocarbon impurities in addition to propylene oxide.

As the distillation and rectification, publicly known methods can be applied.

As an example of a specific method thereof, U.S. Publication No. 2005082159 can be quoted.

In that case, the extractant A separated can be recycled.

By the present invention, purified propylene oxide of a methyl formate content of less than 10 ppm by weight can be obtained.

When water-soluble aldehyde such as formaldehyde, acetaldehyde and propionaldehyde, alcohols such as methanol and propylene glycol, esters such as methyl acetate and organic acids such as formic acid and acetic acid as impurities are contained in propylene oxide containing methyl formate, these impurities can be also removed outside the system by transferring those to the aqueous layer through the above-described operation.

In the above-described operation, propylene oxide simultaneously dissolves in the aqueous layer, therefore, is also lost.

For reducing the loss of propylene oxide in the aqueous layer, preferably, propylene oxide can be selectively extracted to an extractant side (oil layer) by contacting an extractant (an extractant for extracting propylene oxide from the aqueous layer, herein-after, referred to as "extractant B"). The loss of propylene oxide can be reduced by recovering propylene oxide from this oil layer. Further, the loss of propylene oxide may be reduced by recycle the oil layer to the extractive distillation column. However, in this case, since methyl formate is distributed to both sides of the extractant layer and the aqueous layer, methyl formate is concentrated in the system when the extractant is re-used and remains in propylene oxide recovered from the extractant side. The present inventors found that the loss of propylene oxide caused to hydration or the like could be significantly reduced, further, methyl formate was not concentrated in the extractant B because methyl formate was decomposed and removed to the aqueous layer, by adjusting the aqueous layer after separation operation, namely, the aqueous layer described above to be removed outside the system between pH 7 and 9, thereafter, contacting the aqueous layer with the extractant B.

This method can be preferably applied when propylene oxide dissolved in the aqueous layer removed outside the system, is recovered. But, without limiting to this case, the method can be applied to an aqueous layer obtained by washing crude propylene oxide containing at least methyl formate with water. Methyl formate can be effectively removed by washing methyl formate with water, namely, by mixing crude propylene oxide with water, separating into an oil layer and an aqueous layer, and then, adjusting a pH of the obtained aqueous phase to 7 to 9 followed by contacting with an extractant.

Herein, it is preferable for thoroughly mixing water with crude propylene oxide to use a commercially available mixing apparatus such as a stirrer, a static mixer or a line mixer. Further, as an oil-water separating apparatus used for oil-water separation, a common drum or coalescer can be used, but the apparatus is not particularly limited if it can sufficiently separate into an oil and water by still standing. A drum-type oil-water separating apparatus commonly used is preferable.

Washing with water may be carried out according to a one-stage or multi-stage method to obtain the aqueous layer.

When the washing is carried out by a multi-stage method, an aqueous layer obtained at the latter stage may be recycled and used for water washing at the preceding stage. A washing temperature is usually 5 to 100° C., preferably 5 to 50° C. An amount of water supplied is not particularly limited, but it is usually 0.001 to 10 times by weight propylene oxide supplied.

When the temperature is too high, a loss may be large for thermal degradation of propylene oxide, and when it is too low, the performance of oil-water separation may deteriorate. When the amount of water supplied is too small, an efficiency of impurity removal becomes low, on the other hand, when it is too large, there is a tendency of increasing a disposal cost of wastewater because of increasing of a water discharge amount.

Though, as water to be supplied, to supply water containing propylene oxide is effective in recovery of propylene oxide contained in the aqueous layer and preferable, water may not contain propylene oxide.

As a method of adjusting a pH of the above-described aqueous layer or an aqueous layer to be removed outside the system, there can be employed a method of using an acidic reagent or alkaline reagent, or of contacting with an ion-exchange resin. The pH of the aqueous layer is preferably between 7 and 9. When the pH is acidic side beyond this range, a loss of propylene oxide becomes larger because of a formation of propylene glycol by hydration of propylene oxide and a removal efficiency of methyl formate is also low. On the other hand, when the pH of the aqueous layer is too high, a loss of propylene oxide also becomes larger because of a formation of propylene glycol by hydration of propylene oxide. Usually, since the aqueous layer is acidic, it is adjusted with the alkaline reagent. As the alkali reagent, an alkali metal compound such as NaOH or KOH, an alkaline earth metal compound, or alkali metal carbonate such as $Na_2CO_3$ or $NaHCO_3$, ammonia, or $(NH_4)_2CO_3$ is used.

It is preferable to use an alkali metal carbonate of relatively weak alkaline such as $Na_2CO_3$ to avoid unduly increasing of the pH.

The extractant B used for mixing with the aqueous layer in which the pH has been adjusted to 7 to 9, subsequently for removing methyl formate from propylene oxide, preferably includes hydrocarbons having a saturated humidity at 20° C. of 5000 ppm by weight or less such as aliphatic hydrocarbons such as propylene, butane, pentane, hexane, heptane and octane; aromatic hydrocarbons such as ethylbenzene, cumene, toluene, xylene and benzene; and the like. Aliphatic hydrocarbons having 3 to 10 carbon atoms are more preferable because of small in the saturated humidity. Further aliphatic hydrocarbons having 7 to 10 carbon atoms are particularly preferable because those can be used as the extractant A described above. Furthermore, it is the most preferable in efficiency that the extractant A used in the extractive distillation and the extractant B used for contacting and mixing with the aqueous layer described above are the same each other.

Besides, as a method of recovering propylene oxide in the aqueous layer with the extractant B, the aqueous layer containing propylene oxide and impurities is mixed with the extractant B followed by oil-water separation. An apparatus used for the oil-water separation and conditions of the oil-water separation are substantially the same as those in the oil-water separation of crude propylene oxide and water.

Namely, as mixing apparatus, a commercially available common mixing apparatus such as a stirrer, static mixer or line mixer can be used. Further, as an oil-water separating apparatus used for oil-water separation, a common drum or coalescer can be used, but the apparatus is not particularly limited if it can sufficiently separate into an oil and water by still standing.

An oil-water separating operation (herein-after, sometimes referred to as "washing") may be carried out according to a one-stage or multi-stage method. When the washing is carried out by a multi-stage method, an aqueous layer obtained at the latter stage may be recycled and used for water washing at the preceding stage. A washing temperature is usually 5 to 100° C., preferably 5 to 50° C. An amount of water supplied is not particularly limited, but it is usually 0.001 to 10 times by weight propylene oxide supplied. When the temperature is too high, a loss may be large for thermal degradation of propylene oxide, and when it is too low, the performance of oil-water separation may deteriorate. When the amount of water supplied is too small, an efficiency of impurity removal becomes low, on the other hand, when it is too large, there is a tendency of increasing a disposal cost of wastewater because of increasing of a water discharge amount. Therefore, the conditions may be properly selected taking account of these.

As described above, when the reaction mixture containing propylene oxide obtained by reacting a peroxide with propylene contains hydrocarbons having 3 to 7 carbon atoms such as propylene, butane pentane and hexane; water; alcohols such as methanol and propylene glycol, aldehydes such as formaldehyde, acetaldehyde, propionaldehyde; organic acids; ketones such as acetone; and esters such as methyl acetate, it is more preferable to be applied to crude propylene oxide in which the above-described impurities are reduced through rough separation with a distillation column prior to a separation operation according to the extractive distillation or washing with water because an efficiency of oil-water separation increases and a loss of an effective component such as propylene oxide can be reduced.

Particularly, as described above, the aqueous layer obtained by adding water to the overhead distillate of the extractive distillation and then separating into the oil layer and aqueous layer, is removed outside the system, but the loss of propylene oxide can be further reduced by, preferably, adjusting a pH of this aqueous layer to 7 to 9, transferring propylene oxide in the aqueous layer to the extractant side, and then recycling this to the extractive distillation column.

EXAMPLE

Next, the present invention will be described by Examples.

Example 1

Propylene oxide obtained by reacting cumene hydroperoxide with propylene in the presence of a titanium-containing silicon oxide catalyst was used. Fifty ppm by weight of methyl formate was contained in propylene oxide. Propylene oxide was subjected to extractive distillation using n-heptane as an extractant. 3.4 parts by weight of n-heptane per 1 part of propylene oxide were used. As an extractive distillation column, a trays type column was used, and the operation was carried out under conditions of a bottom temperature of 103° C., a overhead temperature of 85° C. and a overhead pressure of 220 kPa. Water was added to a distillate discharged from the overhead of the extractive distillation column to carry out an oil-water separation operation, an oil layer separated was recycled to the extractive distillation column, on the other hand, an aqueous layer separated was removed outside the system. The amount of water added was 0.06 parts by weight. A concentration of methyl formate in the aqueous layer separated was 750 ppm by weight. As a bottom liquid of the extractive distillation column, a mixed liquid of propylene oxide and n-heptane having a methyl formate concentration of 1 ppm by weight, was obtained. The obtained mixed liquid was further subjected to distillation to separate n-heptane, and propylene oxide having a methyl formate concentration of 5 ppm by weight.

Example 2

20 g of an aqueous solution containing 5.3% by weight of propylene glycol (PG), 420 ppm by weight of methyl formate and a small amount of an organic acid, was adjusted to a pH of 8.2 by $Na_2CO_3$, 30 g of an n-heptane solution containing 480 ppm by weight of methyl formate and 4.6% by weight of propylene oxide (PO) was mixed therewith in a 150 ml-flask at 27° C. for 3 minutes followed by still standing to subject to oil-water separation. Amounts of propylene glycol and methyl formate in the oil layer and the aqueous layer were shown in Table 1. Besides, propylene glycol increased by hydration of propylene oxide is calculated as a loss of propylene oxide.

TABLE 1

|  | Example 2 | Example 3 |
|---|---|---|
| pH of aqueous layer Raw material | 8.2 | 8.8 |
| PG (mmol) | 13.9 | 13.9 |
| Methyl formate (mmol) | 0.38 | 0.38 |
| After still standing (oil layer) |  |  |
| PG (mmol) | 0.00 | 0.00 |
| Methyl formate (mmol) | 0.03 | 0.01 |
| After still standing (aqueous layer) |  |  |
| PG (mmol) | 14.5 | 15.4 |
| Methyl formate (mmol) | 0.00 | 0.00 |
| After still standing (total) |  |  |
| PG (mmol) | 14.5 | 15.4 |
| Methyl formate (mmol) | 0.03 | 0.01 |
| PO loss (%) | 2.5 | 6.3 |
| Residual Ratio of methyl formate in oil layer (%) | 7.9 | 2.6 |

Example 3

Example 2 was carried out except that the pH of the aqueous solution was changed to 8.8. Results are shown in Table 1.

Comparative Example 1

Example 2 was carried out except that the pH of the aqueous solution was changed to 6.2. Results are shown in Table 2.

TABLE 2

|  | Comparative Example 1 | Comparative Example 2 |
|---|---|---|
| pH of aqueous layer Raw material | 6.2 | 3.3 |
| PG (mmol) | 13.9 | 13.9 |
| Methyl formate (mmol) | 0.38 | 0.38 |
| After still standing (oil layer) |  |  |
| PG (mmol) | 0.00 | 0.00 |
| Methyl formate (mmol) | 0.09 | 0.07 |
| After still standing (aqueous layer) |  |  |
| PG (mmol) | 14.9 | 22.7 |
| Methyl formate (mmol) | 0.24 | 0.19 |
| After still standing (total) |  |  |
| PG (mmol) | 14.9 | 22.7 |
| Methyl formate (mmol) | 0.33 | 0.26 |
| PO loss (%) | 4.2 | 37 |
| Residual Ratio of methyl formate in oil layer (%) | 24 | 18 |

Comparative Example 2

Example 2 was carried out except that the pH was 3.3 without pH adjustment. Results are shown in Table 2.

INDUSTRIAL APPLICABILITY

According to the present invention, there can be provided, in a method for purifying propylene oxide containing methyl formate as an impurity, a method for purifying propylene oxide having an excellent feature which can obtain propylene oxide in which a methyl formate concentration was reduced by efficiently separating and removing methyl formate as an impurity.

The invention claimed is:

1. A method of purifying propylene oxide, which comprises the following steps:
    (1) subjecting propylene oxide containing methyl formate as an impurity to extractive distillation using a hydrocarbon of 7 to 10 carbon atoms as an extractant with an extractive distillation column,
    (2) adding water to the distillate from the overhead of the extractive distillation column followed by separating into an oil layer and an aqueous layer,
    (3) recycling the oil layer to the extractive distillation column,
    (4) removing the aqueous layer outside the system, contacting the aqueous layer with the same extractant used in the extractive distillation, subsequently separating into an oil layer and an aqueous layer, and supplying the oil layer to an extractive distillation column, and
    (5) obtaining propylene oxide in which a methyl formate concentration is reduced, as a bottom liquid of the extractive distillation column.

2. The method according to claim 1, wherein the propylene oxide subjected to the purification is propylene oxide obtained by reacting cumene hydroperoxide with propylene in the presence of an epoxidation catalyst.

3. The method according to claim 1, wherein the extractant is an aliphatic hydrocarbon having 7 to 10 carbon atoms.

4. The method according to claim 3, wherein the extractant is n-heptane.

5. The method according to anyone of claims 1 to 4, further comprises separating propylene oxide by distilling the bottom liquid of the extractive distillation column.

6. The method according to anyone of claims 1 to 4, further comprises adjusting a pH of the aqueous layer containing propylene oxide removed outside the system to 7 to 9 followed by contacting the aqueous layer with an extractant, subsequently separating into an oil layer and an aqueous layer, and supplying the oil layer to an extractive distillation column.

7. The method according to anyone of claims 1 to 4, further comprises separating propylene oxide by distilling the bottom liquid of the extractive distillation column.

* * * * *